US00PP13683P29

(12) United States Plant Patent
Lyrene

(10) Patent No.: US PP13,683 P2
(45) Date of Patent: Mar. 25, 2003

(54) BLUEBERRY PLANT CALLED 'SEBRING'

(76) Inventor: Paul M. Lyrene, University of Florida P.O. Box 110690, Gainesville, FL (US) 32611-0690

( * ) Notice: Subject to any disclaimer, the term of this patent is extended or adjusted under 35 U.S.C. 154(b) by 0 days.

(21) Appl. No.: 09/981,075

(22) Filed: Oct. 18, 2001

(51) Int. Cl.[7] ..... A01H 5/00

(52) U.S. Cl. ..... Plt./157

(58) Field of Search ..... Plt./157

*Primary Examiner*—Bruce R. Campell
*Assistant Examiner*—June Hwu

(57) ABSTRACT

A new and distinct low-chill southern highbush blueberry (Vaccinium) variety of complex ancestry, based largely on *V. corymbosum* L. with some genes from *V. darrowi* Camp. Its novelty consists of the following unique combination of features.

1. Has a very low chilling requirement.
2. Flowers, produces new leaves, and ripens very early in the year if planted in central Florida where the mean January temperature averages about 63° F.
3. Averages 50% ripe about April 20 in Sebring, Fla. and about May 1 in Gainesville, Fla.
4. Produces a vigorous, upright bush with medium to good survival in the field.
5. Produces berries that are medium to large, medium-blue in color, and have good firmness, good flavor and a medium to good picking scar.

4 Drawing Sheets

CROSS-REFERENCE TO RELATED APPLICATIONS

None.

STATEMENT AS TO RIGHTS TO INVENTIONS MADE UNDER FEDERALLY-SPONSORED RESEARCH

None.

LATIN NAME OF THE GENUS AND SPECIES OF THE PLANT CLAIMED

Vaccinium hybrid.

VARIETY DENOMINATION

Sebring.

BACKGROUND OF THE INVENTION

'Sebring' is a southern highbush blueberry clone with very low chilling requirement that is intended for production of fresh-market blueberries in areas where mean January temperatures average as high as 63° F. 'Sebring' is a complex interspecific hybrid that was produced in a recurrent selection breeding program at the University of Florida in which genes for large berry size, high berry quality, and upright growth habit from *Vaccinium corymbosum* were being combined with genes, derived from *Vaccinium darrowi*, which impart summer heat tolerance, low chilling requirement, and adaptation to other features of the Florida environment. The seed that gave rise to 'Sebring' was produced by hand pollination of the variety 'Sharpblue' (unpatented) with pollen from the variety 'O'Neal' (unpatented). 'Sharpblue', a leading southern highbush variety in Florida, has a low chilling requirement and a large, well-flavored berry, but it ripens over an extended (8-week or more) period, has a wet picking scar and skin that often tears as the berry is picked, has dried corollas that frequently adhere to the ripe berry, and is highly susceptible to blueberry rust and other fungal leaf spots. 'O'Neal', a variety developed at North Carolina State University, produces a large, firm berry with a good picking scar, but its chilling requirement is too high to permit commercial production in Florida. When grown in Florida, O'Neal does not produce enough new leaves in the spring to support a full crop of berries.

'Sebring' was selected in 1983 from a field nursery in Gainesville, Fla., based on high fruit quality, early ripening, and low chilling requirement. The seedling was propagated from softwood cuttings, and an 8-plant plot was established in the field in Gainesville, Fla. in 1987. In 1988, 'Sebring' was again propagated by cuttings, and 10-plant plots were established at each of three other sites in north and central Florida. From these tests it was determined that 'Sebring' flowers, leafs, and fruits early and reliably, even in central Florida, and even after winters when temperatures are above normal. 'Sebring' produces an upright bush with flowers borne on stout twigs. The berry is about the same size as the 'Sharpblue' berry, but the ripening period is more concentrated and berry size does not decline as much after mid-season as with 'Sharpblue'. Because the scar is somewhat better for the 'Sebring' berry and because the dried corollas are not retained on the ripe berry, 'Sebring' berries can be packed for the fresh market with less trouble than 'Sharpblue' berries. It is expected that the main use for 'Sebring' will be for early fresh-fruit production in areas with very mild winters when planted with other very low-chill varieties for cross pollination.

'Sebring' is stable and can be reproduced true-to-type from softwood cuttings. Several hundred plants that were propagated by cuttings at the University of Florida in Gainesville and several thousand plants propagated by cuttings at Payne Blueberry Farm, Sebring, Fla., have been grown to the age of fruiting and have shown no deviation from the characteristics of the clone.

SUMMARY OF THE INVENTION

'Sebring' has the following novel combination of characteristics that set it apart from other blueberry varieties.

a. It flowers and produces an abundance of new leaves in late winter or early spring when grown where mean January temperatures are as high as 63° F.

b. It produces medium to large, firm berries with a medium to dry scar and a sweet, subacid flavor.

c. It is upright in growth habit, produces stout canes and has limited twigginess.

d. It roots readily from softwood cuttings.

e. When grown in north-central Florida (mean January temperature 56° F.) the average date of 50% flowering is February 15 and the average date of 50% ripe fruit is May 1.

f. The berry is medium to light blue in color.

g. The clone is tetraploid, with a somatic chromosome number of 48.

h. 'Sebring' has moderately good resistance to Phytophthora root rot and good resistance to stem blight (*Botryosphaeria dothidia*) and cane canker (*Botryosphaeria corticis*).

BRIEF DESCRIPTION OF THE DRAWINGS

The color chart used in this specification is "The Pantone Book of Color", by Leatrice Eiseman and Lawrence Herbert. 1990. Harry N. Abrams, Inc., Publishers, N.Y. The colors in these drawings are as accurate as they can be given the photographic techniques used. Where colors in the drawings differ from the Pantone color designations in the verbal descriptions, the Pantone color designations are the more accurate.

The first drawing shows several plants of 'Sebring' approximately 1.9 m tall growing in pine bark in a field near Gainesville, Fla. in May, 2001. The upright growth habit, the tendency of the plant to sprout moderately from the base, and the overall arrangement of the leaves and fruit are visible.

The second drawing shows at close view a cluster of 'Sebring' flowers, including the white corollas and some styles from which the corollas have shed following pollination.

The third drawing shows at close view the shape and arrangement of the leaves and a cluster of ripe berries of 'Sebring'.

The fourth drawing shows the ripe berries of 'Sebring' in two orientations. Berries in the center column and in the column on the left are arranged to show the calyx aperatures of the berries and the poorly developed calyx lobes. The four berries in the column on the right show the picking scar, left when the berry separates from the pedicel. The pedicel-attachment scars are small to medium in size, with only occasional skin tears.

BOTANICAL DESCRIPTION OF THE PLANT

'Sebring' is a complex interspecific hybrid derived from the cross 'Sharpblue' (unpatented)×'O'Neal' (unpatented). The principal species involved in breeding 'Sebring' were *Vaccinium corymbosum* and *V. darrowi*. The genes of the two parental species were sorted through several generations of crossing and selection to produce 'Sebring'. 'Sebring' does not correspond to any pure botanical species. The commercial value of 'Sebring' lies in the fact that the clone can be grown in central Florida without suffering from lack of winter chilling. This allows a very early harvest of berries from 'Sebring'. Various characteristics of 'Sebring' are described below.

Market class: 'Sebring' produces blueberries that are suited to the fresh fruit market.

Bush: Plant characteristics were measured on 3-year-old plants planted in pine bark beds in Gainesville, Fla. at a 1 m×1.5 m spacing. The plants had been fertilized and watered as on commercial blueberry farms in Florida.

*Plant height.*—1.9 m.

*Canopy diameter measured at widest part of bush.*—1.2 m.

*Plant vigor.*—High. Equal to 'Sharpblue' (unpatented).

*Growth habit.*—Upright.

*Flower bud density (number) along flowering twigs in January.*—Medium. Somewhat less than for 'Sharpblue'.

*Twigginess.*—Low. Twigs tend to be stout and limited in number.

Trunk:

*Suckering tendency.*—Medium. Average of 10 major canes rising from the base of 3-year-old plants.

*Surface texure of strong, 6-month old stems observed August 1.*—Smooth.

*Surface texture of strong, 1-year-old shoots observed August 1.*—Changing from smooth to rough.

*Surface texture of 3-year-old wood.*—Rough, but exfoliating to smooth.

*Color of 6-month-old wood on strong shoots viewed August 1.*—"Dried moss", Pantone 14-0626.

*Color of 1-year-old smooth wood viewed August 1.*—"Golden ochre", Pantone 16-1346.

*Color of 3-year-old rough-textured canes viewed August 1.*—"Sesame", 15-1215.

*Color of current season twigs viewed August 1.*—"Aragon", 17-1532.

*Surface texture of current-season twigs.*—Smooth.

*Internode length on strong, upright shoots measured August 1.*—Mean 1.7 cm.

Leaves:

*Leaf length.*—Note: leaves are highly variable in size. The leaves that were measured were the largest 25% on lateral shoots exposed to full sun. Leaf length included the petiole and extended from the tip of the petiole to the end of the blade. Mean. 7.3 cm.

*Leaf width at widest point.*—Mean 4.6 cm.

*Leaf shape.*—Oval. Tip acute with a pronounced dew tip about 0.5 mm long visible at 30× magnification.

*Leaf margin.*—Entire.

*Color of upper surface of leaves.*—"Periodot", 17-0336.

*Color of lower surface of leaves.*—"Tarragon", 15-0326.

*Pubescence on upper surface of leaves.*—Short, white hairs on midrib of the upper surface visible at 30× magnification.

*Pubescence on lower surface of leaves*—Sparse indumentum of short, white hairs along basal half of midrib on underside of leaf is visible at 30× magnification.

*Pubescence on leaf margins.*—Viewed from the underside of the leaf, there is a sparse line of, white hairs along the basal one-third of the leaf margin.

Flowers:

*Flower arrangement.*—Flowers arranged alternately along a short, leafless, deciduous branch.

*Fragrance.*—Slight honeysuckle fragrance.
*Pedicel length at time of anthesis.*—Mean 5.6 mm.
*Peduncle length at time of anthesis.*—Mean 10.7 mm.
*Petals.*—Fused into a corolla tube with 5 lobes.
*Pollen staining.*—Approximately 99% of the grains stain with acetocarmine dye, indicating that a very high percentage of the pollen grains are normal, plump, and potentially viable.
*Pollen abundance.*—Dried flowers shed pollen abundantly.
*Pollen color.*—Color of dried pollen. "Straw", Pantone 13-0902.
*Flower type.*—Perfect, ovary inferior, petals fused into a corolla tube, the 10 stamens inserted at the base of the corolla tube.
*Flower length, pedicel attachment point to corolla tip.*—Mean 11.7 mm.
*Style length, top of ovary to stigma tip.*—Mean 9.5 mm.
*Calyx diameter at anthesis, tip of lobe to tip of opposite lobe.*—Mean 5.4 mm.
*Diameter of corolla tube at widest point.*—Mean 8.7 mm.
*Corolla aperture diameter.*—Mean 3.7 mm.
*Corolla surface texture.*—Smooth.
*Flower shape.*—Cylindrical.
*Corolla color at anthesis.*—"Snow white", Pantone 11-0602.
*Calyx color at anthesis.*—"Nile", Pantone 14-0223.
*Flowering period.*—Mean date of 50% open flower in Gainesville, Fla. February 15.
*Flower cluster (tight, medium, or open).*—Medium.
*Number of flowers per cluster.*—Mean 7.8 . Self fruitfulness.
*Location of tip of style relative to lip of corolla.*—Tip of stigma is even with the tip of the corolla tube.

Berry:
*Mean date of 50% fruit ripe in Gainesville, Fla.*—May 1.
*Diameter of calyx aperture on mature berry.*—5 to 6 mm.
*Calyx lobes on mature berry: size and shape.*—Calyx aperture slightly recessed on ripe berry. Calyx lobes on ripe berry small, irregular, poorly developed.
*Berry cluster (tight, medium, or open).*—Medium.
*Pedicel length of ripe berry.*—Mean 5.6 mm.
*Peduncle length of ripe berries.*—Mean 10.7 mm.
*Mean number of ripe berries per cluster.*—5.9.
*Mean berry weight on well-pruned plants.*—2.0 g.
*Mean berry height.*—10 mm.
*Mean berry width.*—14 mm.
*Berry color (ripe) on plant.*—"Steel gray", Pantone 18-4005.
*Berry color after harvest and modest handling.*—"Dark Gull Gray", Pantone 18-0403.
*Berry skin color after polishing.*—"Jet black", Pantone 19-0303.
*Internal flesh color of ripe berry.*—"Frozen dew", Pantone 13-0513.
*Berry surface wax.*—Rather sparse. Below average persistence when berries handled.
*Berry pedicel scar.*—Small to medium diameter, usually dry but occasionally tearing when berries very ripe.
*Berry firmness.*—Medium to high. Firmer than 'Sharpblue' (not patented).
*Berry flavor.*—Sweet, subacid, pleasant.
*Berry texture.*—Small seeds, not gritty.
*Color of dried seeds.*—"Beige", Pantone 14-1118.
*Weight of well-developed dried seeds.*—0.62 mg per seed.
*Length of well-developed seed.*—2.0 mm.
*Width of well-developed seed.*—1.1 mm.

Physiological characteristics:
*Chilling requirement.*—200 hours per winter below 7° C. are required for full bud break.
*Cold hardiness.*—Flowers and berries are hardy to −3° C. The plant, during winter dormancy, is hardy to −15° C.
*Productivity.*—'Sebring' yields about 6 metric tons per hectare per year on good sites.

Diseases, insects, mites:
*Phytophthora root rot.*—Medium resistant. Slightly more susceptible than 'Sharpblue' (unpatented).
*Stem blight (Botryosphaeria dothidia).*—Medium resistant. Slightly more susceptible than 'Sharpblue' (unpatented).
*Stem canker (Botryosphaeria corticis).*—Resistant to the common races.
*Fungal and bacterial leaf spots.*—Resistance about average. Fungicide sprays may be needed in summer to maintain leaf in commercial plantings.
*Blueberry bud mites.*—Above average resistance.
*Overall survival in the field.*—Medium to good. Slightly more plant loss than for 'Sharpblue' (unpatented) on similar sites.

Ease of propagation: 'Sebring' propagates readily from softwood cuttings.

I claim:

1. A new and distinct highbush blueberry plant, substantially as illustrated and described, characterized by a very low chilling requirement, early flowering, early ripening, and a high-quality, medium to large berry.

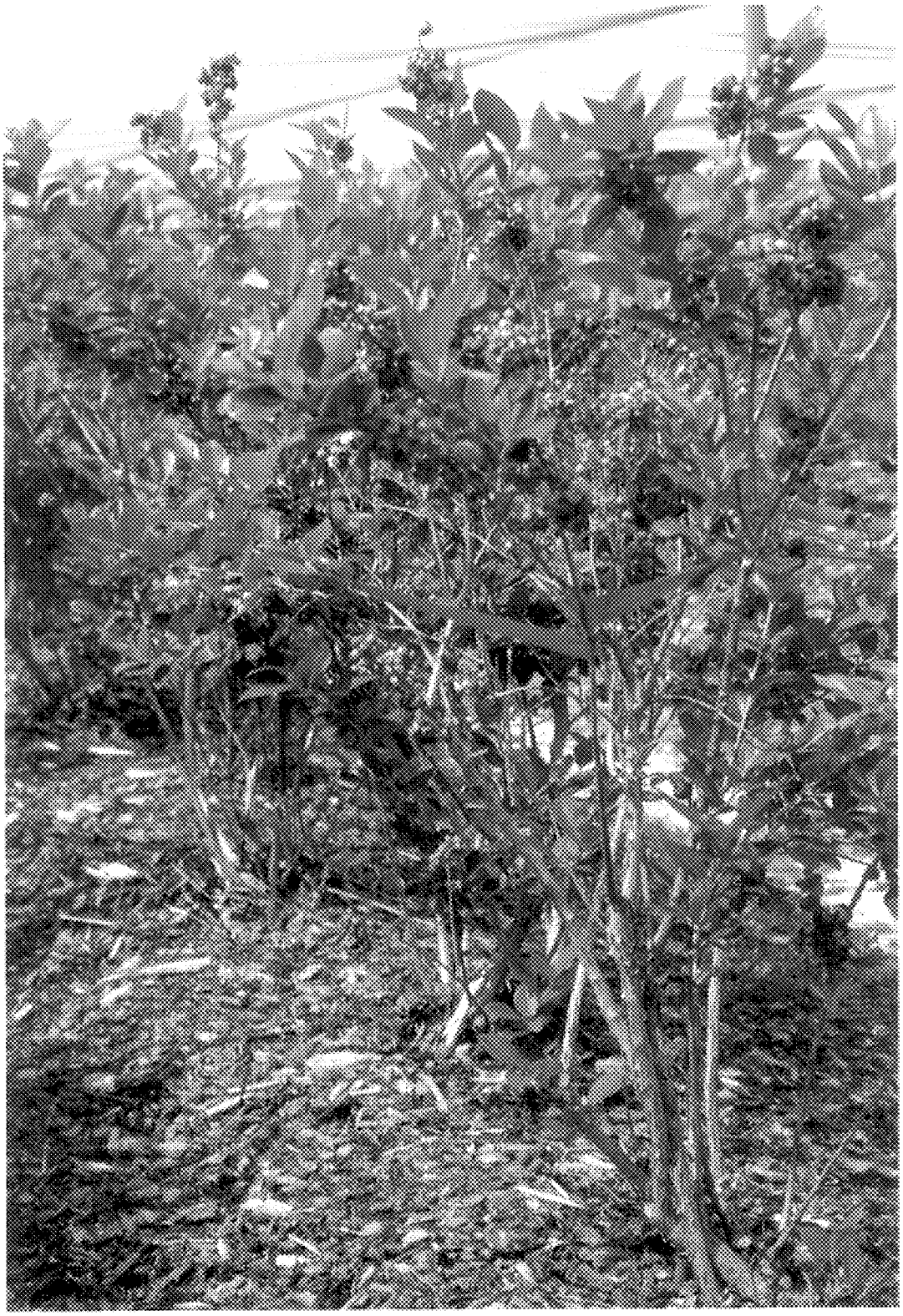

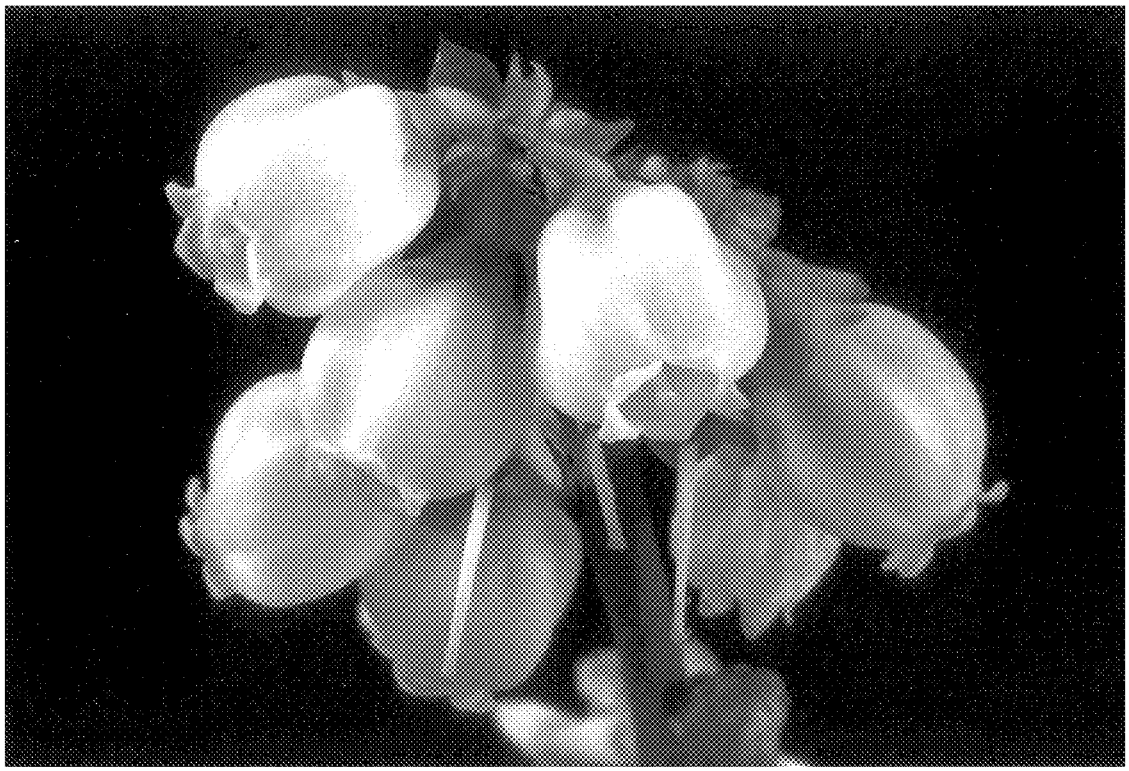

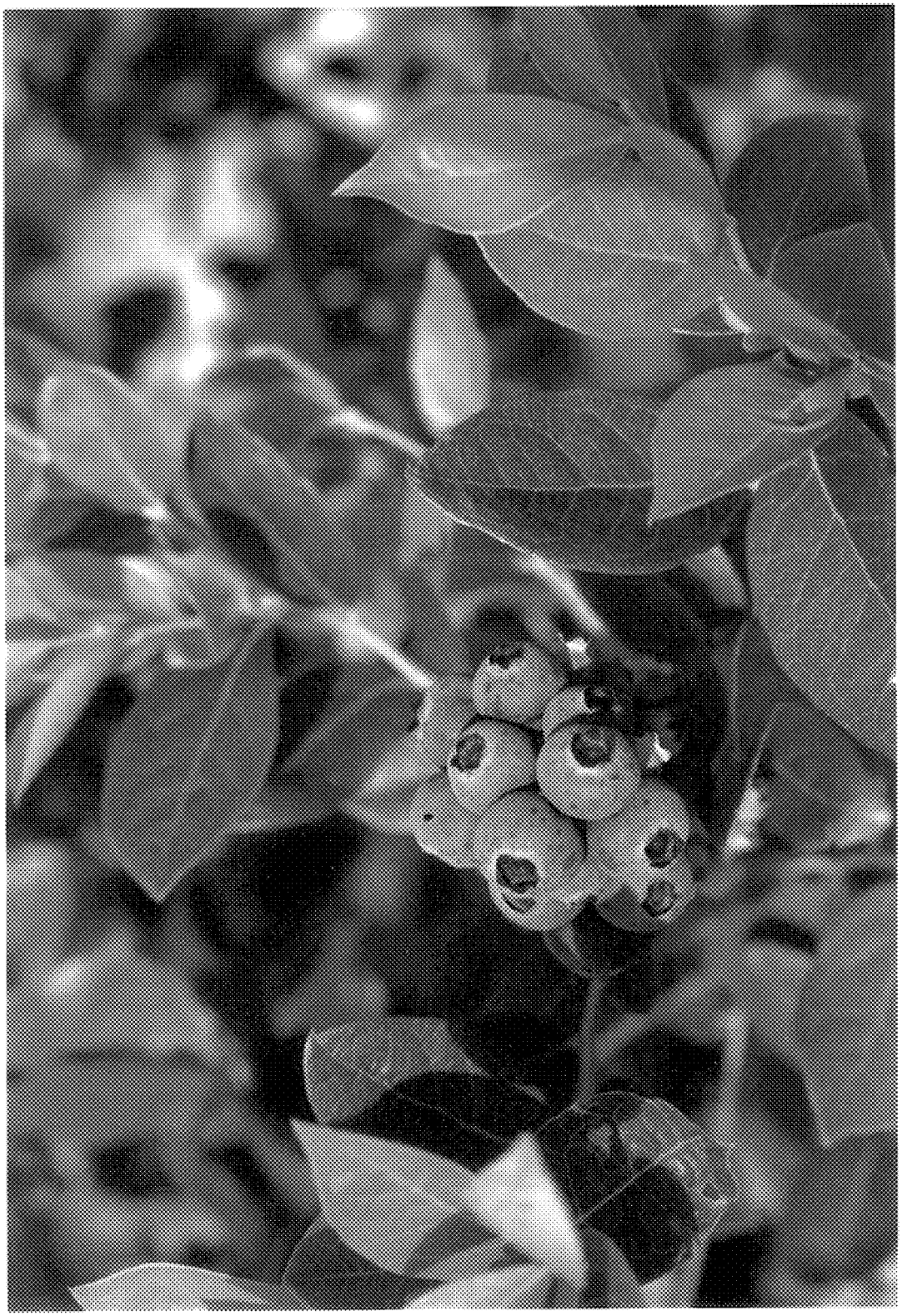

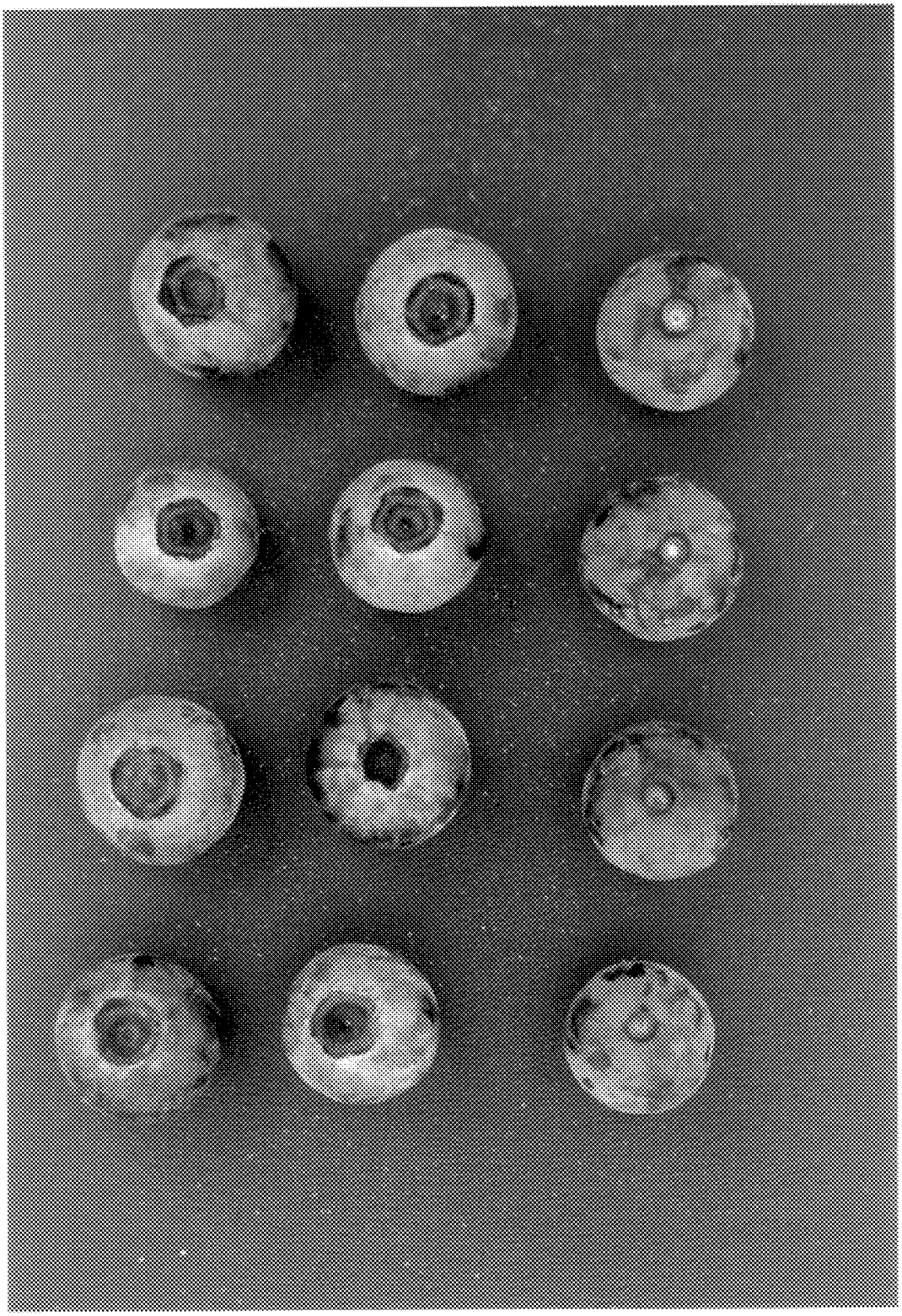

* * * * *